United States Patent [19]

Panoz et al.

[11] Patent Number: 4,826,688

[45] Date of Patent: May 2, 1989

[54] CONTROLLED ABSORPTION PHARMACEUTICAL FORMULATION

[75] Inventors: Donald E. Panoz, Tuckerstown, Bermuda; Edward J. Geoghegan, Athlone, Ireland

[73] Assignee: 501 Elan Corporation PLC., Athlone, Ireland

[21] Appl. No.: 930,138

[22] Filed: Nov. 12, 1986

[30] Foreign Application Priority Data

Nov. 13, 1985 [IE] Ireland .................... 2842/85

[51] Int. Cl.$^4$ .................... A61K 9/22; A61K 9/52
[52] U.S. Cl. .................... 424/458; 424/461; 424/462; 424/468; 424/469; 424/470
[58] Field of Search ............ 424/468, 478, 473, 469, 424/470, 480, 482

[56] References Cited

U.S. PATENT DOCUMENTS

| | | | |
|---|---|---|---|
| 4,341,759 | 7/1982 | Bogentoft et al. | 424/494 |
| 4,361,546 | 11/1982 | Stricker et al. | 424/280 |
| 4,432,965 | 2/1984 | Keith et al. | 424/482 |
| 4,443,428 | 4/1984 | Oshlaek et al. | 424/488 |
| 4,459,279 | 7/1984 | Stricker et al. | 424/273 |
| 4,521,401 | 6/1985 | Dunn | 424/480 |
| 4,572,833 | 2/1986 | Pedersen et al. | 424/482 |
| 4,578,264 | 3/1986 | Stricker et al. | 424/462 |
| 4,606,909 | 8/1986 | Beatgaard et al. | 424/482 |
| 4,713,248 | 12/1987 | Kjornaes et al. | 424/470 |
| 4,716,041 | 12/1987 | Kjornaes et al. | 424/469 |

*Primary Examiner*—Shep K. Rose
*Attorney, Agent, or Firm*—Hubbard, Thurman Turner & Tucker

[57] ABSTRACT

A controlled absorption quinidine formulation for oral administration comprises a pellet having a core of quinidine or a pharmaceutically acceptable salt thereof in association with an organic acid and optionally other excipients, and an outer membrane which permits release of quinidine in an aqueous medium at a controlled rate which is substantially pH independent. The pellet has a dissolution rate in vitro, which when measured in a Basket Assembly according to U.S. Pharmacopoeia XXI at 37° C. and 75 r.p.m. is not more than 15% after one hour of measurement. Not more than 50% of the total quinidine is release after a total of 4 hours of measurement, not more than 80% is released after a total of 8 hours of measurement and not less than 90% release is achieved after a total of 24 hours.

15 Claims, 6 Drawing Sheets

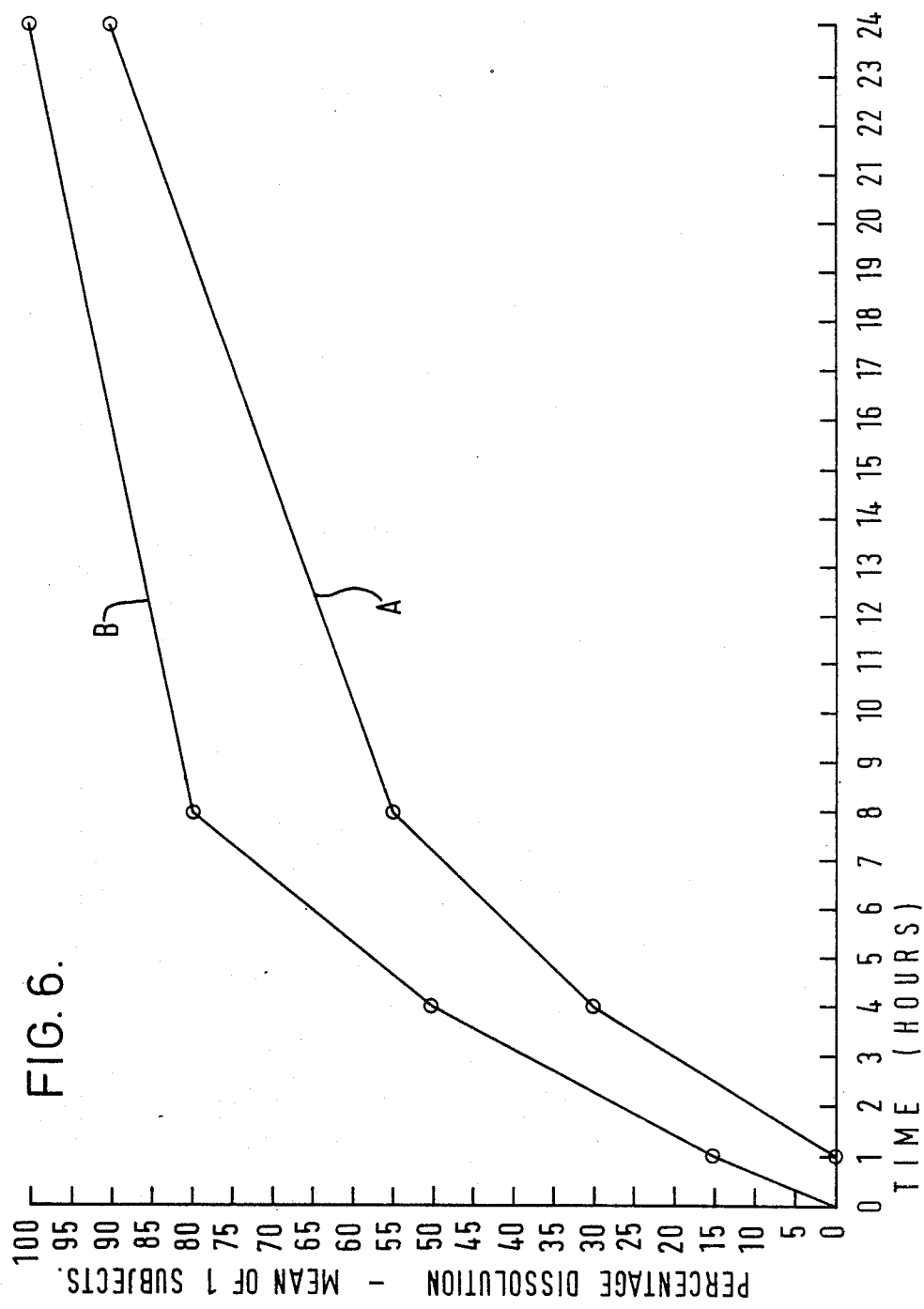

CONTROLLED ABSORPTION PHARMACEUTICAL FORMULATION

BACKGROUND OF THE INVENTION

This invention relates to a controlled absorption pharmaceutical formulation and, in particular, to a controlled absorption quinidine formulation which is suitable for once daily administration.

Quinidine is a cardiac depressant which reduces cardiac activity by directly depressing the excitability of the myocardium and prolonging the refractory period of cardiac muscle, thereby reducing the rate at which successive contractions take place.

Quinidine(($+$)-$\alpha$-(6-methoxyquinolin-4-yl)-$\alpha$-(5-vinylquinuclidin-2-yl)methanol) is normally used in the form of a salt thereof, for example, quinidine gluconate or quinidine sulphate.

Quinidine sulphate is usually rapidly absorbed from the gastro-intestinal tract and peak plasma concentrations are reached in about two hours. About 60% of quinidine in the blood is bound to plasma albumin. Quinidine is almost entirely excreted in the urine; 10–50% is eliminated unchanged within 24 hours of a dose being taken. The half-life of quinidine sulphate is found to be about 6.5 hours in normal subjects.

Quinidex Extentabs (Trade Mark) is a sustained action tablet formulation of quinidine sulphate suitable for twice daily administration. To-date no controlled action quinidine formulation exists which is suitable for once daily administration and which has a high and invariable absorption profile.

It is an object of the present invention to provide a controlled adsorption form of quinidine which is suitable for once daily administration, which is characterised by a high degree of absorption, which is substantially invariable from subject to subject, and by significant plasma levels of quinidine which are maintained for an extended period after administration relative to other sustained release forms of the drug.

SUMMARY OF THE INVENTION

Accordingly, the invention provides a controlled absorption quinidine formulation for oral administration, comprising a pellet having a core of quinidine or a pharmaceutically acceptable salt thereof in association with an organic acid, and a membrane of a film-forming polymer or mixture thereof surrounding the core and which permits release of quinidine at a controlled rate in an aqueous medium, said pellet having a dissolution rate which is substantially pH independent and which when measured in a Basket Assembly according to U.S. Pharmacopoeia XXI at 37° C. and 75 r.p.m. has the following characteristics:

(a) from 0 to 15% of the total quinidine is released after one hour of measurement in said assembly;

(b) from 30 to 50% of the total quinidine is released after four hours of measurement in said assembly;

(c) from 55 and 80% of the total quinidine is released after eight hours of measurement in said assembly; and (d) not less than 90% of the total quinidine is released after twenty-four hours of measurement in said assembly.

DETAILED DESCRIPTION OF THE INVENTION

Figure 1:
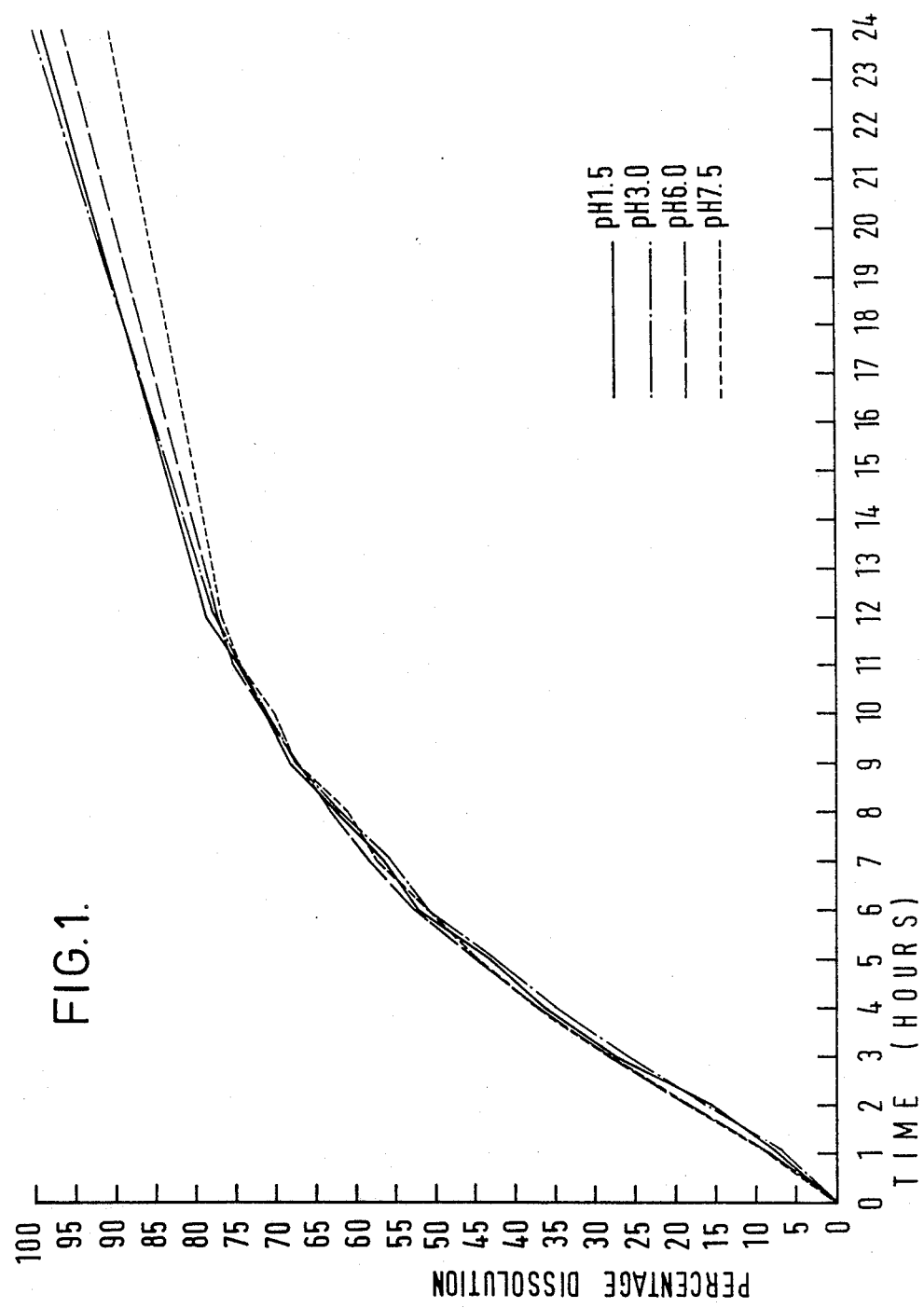

Preferably, the quinidine is in the form of a pharmaceutically acceptable salt thereof. Particularly suitable salts include quinidine gluconate, quinidine disulphate or quinidine sulphate.

The organic acid is preferably represented by one or more of the following acids: adipic acid, ascorbic acid, citric acid, fumaric acid, malic acid, succinic acid or tartaric acid.

The quinidine component and organic acid are preferably present in a ratio of from 1:1 to 10:1 and most preferably at a ratio which permits release of quinidine at a controlled rate in an aqueous medium and at which the pellet has a dissolution rate which is substantially pH independent.

Preferably the core comprises quinidine or a pharmaceutically acceptable salt thereof and the associated organic acid embedded in a polymeric material. The polymeric material may be rapidly soluble in water or, alternatively, may be freely permeable to quinidine and water.

The polymeric material may consist solely of a water soluble polymer or a polymer which is freely permeable to quinidine and water. Alternatively, the polymeric material of the core may include a minor proportion of a water insoluble polymer or a polymer which is slightly permeable to quinidine and water. The ratio of water soluble/freely permeable to water insoluble/slightly permeable polymer is determined by the particular combination of polymers selected.

The water soluble polymer is suitably hydroxypropylmethylcellulose or polyvinylpyrrolidone. A suitable polymer which is freely permeable to quinidine and water is a polymer sold under the Trade Mark Eudragit RL.

The water insoluble polymer is suitably a cellulose ether such as methyl-, ethyl- or propylcellulose or shellac. A suitable polymer which is slightly permeable to quinidine and water is a polymer sold under the trade Mark Eudragit RS.

Eudragit polymers are polymeric lacquer substances based on acrylate and/or methacrylate.

Polymeric materials sold under the Trade Marks EUDRAGIT RL and RS are acrylic resins comprising copolymers of acrylic and methacrylic acid esters with a low content of quaternary ammonium groups and are described in the "EUDRAGIT" brochure of Messrs. Rohm and Haas (1985) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

The core suitably has between 100 and 200 layers and is built up in a manner known per se.

Preferably, the multi-layer arrangement of quinidine, organic acid and polymeric material is built up on a central inert core suitably consisting of a non-pareil seed of sugar or starch having an average diameter in the range of 0.3–3.7 mm, especially 0.4–0.5 mm, in a conventional coating pan or using an automatic coating system such as a Freund CF granulator.

The core may also include other components such as a lubricant, a dispersing agent or a surfactant. A suitable lubricant is talc and a suitable surfactant is sodium lauryl sulphate.

The quinidine or salt thereof, organic acid and optionally other components such as a lubricant are blended to form a homogeneous powder. The blend is suitably passed through a No. 100 mesh screen using a milling machine. Alternate layers of a coating solution/-suspension of the polymeric material and the powder are applied to the central inert core so as to build up the multi-layer arrangement of the active core. The coating solution/suspension of the polymeric material comprises one or more polymers dissolved/suspended in a suitable solvent or mixture of solvents. The concentration of the polymeric material in the coating solution/-suspension is determined by the viscosity of the final solution. A suitable plasticiser such as diethylphthalate may be added to the coating solution. Especially preferred coating solutions/suspensions include:

(a) 7 to 10 parts by volume 10% hydroxypropylmethylcellulose in methanol/methylene chloride 60/40 and 0 to 3 parts by volume 10% ethylcellulose in methanol/methylene chloride 60/40;

(b) 6 to 10 parts by volume 5% Eudragit RL in isopropanol/acetone 60/40 and 0 to 4 parts by volume 5% Eudragit RS in isopropanol/acetone 60/40; and (c) 7 to 10 parts by volume 10% polyvinylpyrrolidone in isopropanol or ethanol and 0 to 3 parts by volume 17.5% shellac in ethanol.

In an automatic coating system, the powders and the solution/suspension are applied separately but simultaneously in conventional manner.

The membrane of the film-forming polymer or mixture of polymers surrounding the core preferably has a major proportion of a water insoluble polymer and a minor proportion of a water soluble polymer, the ratio of water insoluble to water soluble polymer being determined by the inherent solubility characteristics of the polymers selected.

Suitable combinations of water insoluble and water soluble polymers for the membrane include: ethylcellulose and hydroxypropylmethylcellulose in a ratio of from 8:0.25 to 9.75:2; and shellac and polyvinylpyrrolidone in a ratio of from 7.5:0.25 to 9.75:2.5.

The membrane may also be composed of a major proportion of a non-porous polymer and a minor proportion of a porous polymer, the ratio of non-porous to porous polymer being determined by the inherent porosity of the respective polymers.

The membrane may further be composed of a major proportion of a polymer which is slightly permeable to quinidine and water and a minor proportion of a polymer which is freely permeable to quinidine and water the ratio of slightly permeable to freely permeable polymer being determined by the inherent permeability of the respective polymers. A suitable combination of a polymer which is slightly permeable to quinidine and water and a polymer which is freely permeable to quinidine and water is EUDRAGIT RS and EUDRAGIT RL in a ratio of from 7.5:0.5 to 9.5:2.5.

The membrane is built up by applying a plurality of coats of membrane polymer solution or suspension to the core as hereinafter described. The membrane solution or suspension contains the polymer(s) dissolved or suspended, respectively, in a suitable solvent or mixture of solvents, optionally in the presence of a lubricant. Suitable lubricants are talc, stearic acid and magnesium stearate. Preferably the number of coats of membrane solution or suspension applied is between 8 and 30 coats. Further, preferably, 2-25 ml of membrane solution or suspension is applied per kilogram of cores. The membrane solution or suspension may include a suitable plasticiser, such as diethylphthalate.

Especially preferred membrane suspensions include (a) 0.25 to 2 parts by volume 5% hydroxypropylmethylcellulose in methanol/methylene chloride 60/40, 8 to 9.75 parts by volume 5% ethylcellulose in the same solvent, and 5 parts by weight talc.

(b) 0.5 to 2.5 parts by volume 2.5% Eudragit RL in isopropanol acetone 60/40, 7.5 to 9.5 parts by volume 2.5% Eudragit RS in the same solvent, and 5 parts by weight talc.

(c) 0.25 to 2.5 parts by volume 7.5% polyvinylpyrrolidone in isopropanol or ethanol, 7.5 to 9.75 parts by volume 17.5% Shellac in ethanol, and 5 parts by weight talc.

The pellets when prepared may be filled into hard or soft gelatine capsules.

The pellets may also be compressed into tablets using a binder and/or hardening agent commonly employed in tableting such as microcrystalline cellulose sold under the Trade Mark Avicel or a co-crystallised sucrose and modified dextrin powder containing 97% by weight sucrose and 3% by weight modified dextrin sold under the Trade Mark "DI-PAC", in such a way that the specific dissolution rate of the pellets is maintained.

The invention will be further illustrated by the following Examples.

EXAMPLE 1

Quinidine sulphate (40 kg) and fumaric acid (12 kg) were blended and passed through a No. 100 mesh screen using a conventional milling machine.

A polymer solution was prepared containing 9 parts by volume 10% polyvinylpyrrolidone in isopropanol and 1 part by volume 17.5% Shellac in ethanol.

Starch/sugar seeds (0.4 to 0.5 mm diameter) (4 kg) were placed in a standard coating pan and rotation commenced.

The seeds were wetted with sufficient polymer solution to dampen them thoroughly and then an amount of the powder blend was dusted on until no more adhered. This step was repeated until all of the powder blend had been applied. The coated seeds were allowed to dry after each application. When all of the powder blend had been applied the coated seeds were dried at 40°-60° C. until all of the solvent had been driven off.

A membrane suspension was prepared from the following components:

0.5 parts by volume 10% polyvinylpyrrolidone in isopropanol, 9.5 parts by volume 17.5% Shellac in ethanol, and 5 parts by weight talc.

Eighteen "coats" of the membrane suspension were applied to the coated seeds prepared above and which define the active core of the pellets being prepared. The membrane suspension was applied to the coated seeds in the coating pan thereby forming pellets, each coat applied amounting to 10 ml of suspension per kg of coated seeds. After each coat had been applied the coated seeds were air dried in the coating pan.

After the final coat had been applied the pellets were dried at 40°-60° C. to evaporate all traces of solvent.

The finished pellets were then subjected to a dissolution test as follows:

Apparatus: Basket Assembly described in U.S.P. XXI at 37° C. and 75 r.p.m.

Medium: Water

Method: 1 g of pellets was placed in each basket. The test was commenced and 1 ml samples withdrawn at intervals of 1 hour up to 12 hours and then at 24 hours. The sample was diluted to 50 ml with 0.1N hydrochloric acid and the absorbance read in a spectrophotometer. The absorbance value equivalent to 100% dissolution was determined by dissolving 100 mg in sufficient 0.1N hydrochloric acid to make 100 ml, diluting 1 ml to 50 ml with the same solvent and then reading the absorbance.

The percentage dissolution was calculated by dividing the sample absorbance reading by the 100% absorbance reading.

The dissolution test was carried out using solutions of pH 1.5, 3.0, 6.0 and 7.5 to determine the degree of pH dependence. The results are shown in Table 1. A graphic representation of the results is indicated in FIG. 1.

Figure 2:
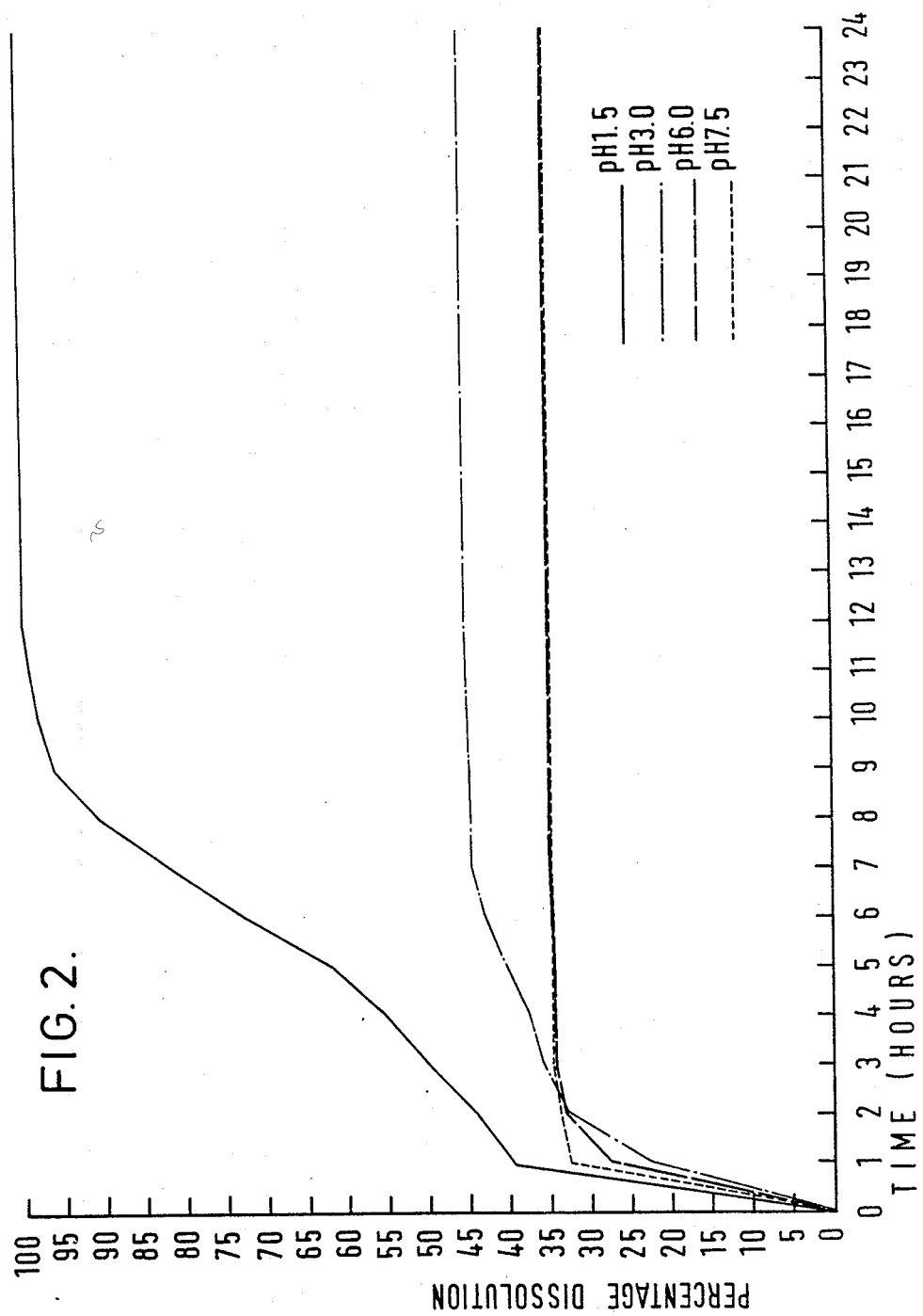

In a comparison study dissolution tests were carried out on a commercially available sustained action formulation of quinidine sulphate viz Quinidex Extentabs (Quinidex Extentabs is a Trade Mark of A. H. Robins & Co. Inc.). The dissolution results for the reference tablets are given in Table 2 and FIG. 2 of the accompanying drawings.

TABLE 1
PELLETS OF EXAMPLE 1
PERCENTAGE DISSOLUTION TIME (HOURS)

| pH | 0.00 | 1.00 | 2.00 | 3.00 | 4.00 | 5.00 | 6.00 | 7.00 | 8.00 | 9.00 | 10.00 | 11.00 | 12.00 | 24.00 |
|---|---|---|---|---|---|---|---|---|---|---|---|---|---|---|
| pH 1.5 | 0.00 | 7.10 | 15.60 | 27.40 | 36.20 | 43.10 | 52.00 | 56.30 | 62.30 | 68.00 | 71.10 | 74.50 | 78.30 | 98.60 |
| pH 3.0 | 0.00 | 6.60 | 16.30 | 26.10 | 35.00 | 42.60 | 51.10 | 55.40 | 61.90 | 67.60 | 71.20 | 73.90 | 77.50 | 99.80 |
| pH 6.0 | 0.00 | 8.20 | 18.30 | 28.00 | 37.10 | 44.80 | 52.70 | 58.20 | 63.00 | 67.10 | 71.10 | 75.10 | 77.10 | 96.10 |
| pH 7.5 | 0.00 | 8.40 | 18.50 | 28.40 | 36.70 | 44.70 | 51.00 | 57.30 | 61.00 | 67.50 | 70.00 | 74.20 | 76.60 | 90.20 |
| MEAN | 0.00 | 7.58 | 17.18 | 27.48 | 36.25 | 43.80 | 51.70 | 56.80 | 62.05 | 67.55 | 70.85 | 74.42 | 77.38 | 96.17 |
| ST DEV | 0.00 | 0.87 | 1.45 | 1.00 | 0.91 | 1.12 | 0.80 | 1.21 | 0.84 | 0.37 | 0.57 | 0.51 | 0.72 | 4.27 |
| *CV (%) | 0.00 | 11.43 | 8.42 | 3.66 | 2.51 | 2.55 | 1.56 | 2.14 | 1.35 | 0.55 | 0.80 | 0.69 | 0.93 | 4.44 |

*coefficient of variation

TABLE 2
REFERENCE QUINIDEX EXTENTABS (TRADE MARK)
PERCENTAGE DISSOLUTION TIME (HOURS)

| pH | 0.00 | 1.00 | 2.00 | 3.00 | 4.00 | 5.00 | 6.00 | 7.00 | 8.00 | 9.00 | 10.00 | 11.00 | 12.00 | 24.00 |
|---|---|---|---|---|---|---|---|---|---|---|---|---|---|---|
| pH 1.5 | 0.00 | 39.30 | 44.00 | 49.90 | 55.20 | 61.90 | 72.60 | 81.65 | 90.39 | 95.99 | 98.00 | 99.00 | 99.99 | 99.99 |
| pH 3.0 | 0.00 | 22.62 | 32.53 | 35.91 | 37.55 | 40.39 | 43.01 | 44.54 | 44.60 | 44.70 | 45.00 | 45.10 | 45.20 | 45.25 |
| pH 6.0 | 0.00 | 27.41 | 33.18 | 34.38 | 34.38 | 34.38 | 34.60 | 34.60 | 34.60 | 34.70 | 34.80 | 34.90 | 35.00 | 35.00 |
| PH 7.5 | 0.00 | 32.40 | 33.62 | 34.60 | 34.70 | 34.70 | 34.70 | 34.70 | 34.70 | 34.70 | 34.70 | 34.70 | 34.80 | 34.80 |
| MEAN | 0.00 | 30.43 | 35.83 | 38.70 | 40.46 | 42.84 | 46.23 | 48.87 | 51.07 | 52.52 | 53.13 | 53.42 | 53.75 | 53.76 |
| ST DEV | 0.00 | 7.13 | 5.46 | 7.50 | 9.93 | 13.00 | 18.02 | 22.34 | 26.63 | 29.36 | 30.30 | 30.77 | 31.21 | 31.20 |
| *CV (%) | 0.00 | 23.44 | 15.25 | 19.38 | 24.55 | 30.25 | 38.98 | 45.72 | 52.14 | 55.90 | 57.04 | 57.59 | 58.06 | 58.04 |

*Coefficient of variation

EXAMPLE 2

Quinidine sulphate (40 kg) and succinic acid (10 kg) were blended and milled through a No. 100 mesh screen. The milled blend was applied to starch/sugar seeds (0.4–0.5 mm diameter) (4 kg) using 8 parts by volume 5% Eudragit RL and 2 parts by volume 5% Eudragit RS in isopropanol/acetone 60/40 as the coating solution, following the procedure described in Example 1.

The coated seeds were surrounded by a membrane by applying 18 coats of a suspension consisting of:
1 part by volume 2.5% Eudragit RL,
9 parts by volume 2.5% Eudragit RS, and
5 parts by weight talc.

The membrane was applied following the procedure set forth in Example 1.

Figure 3:
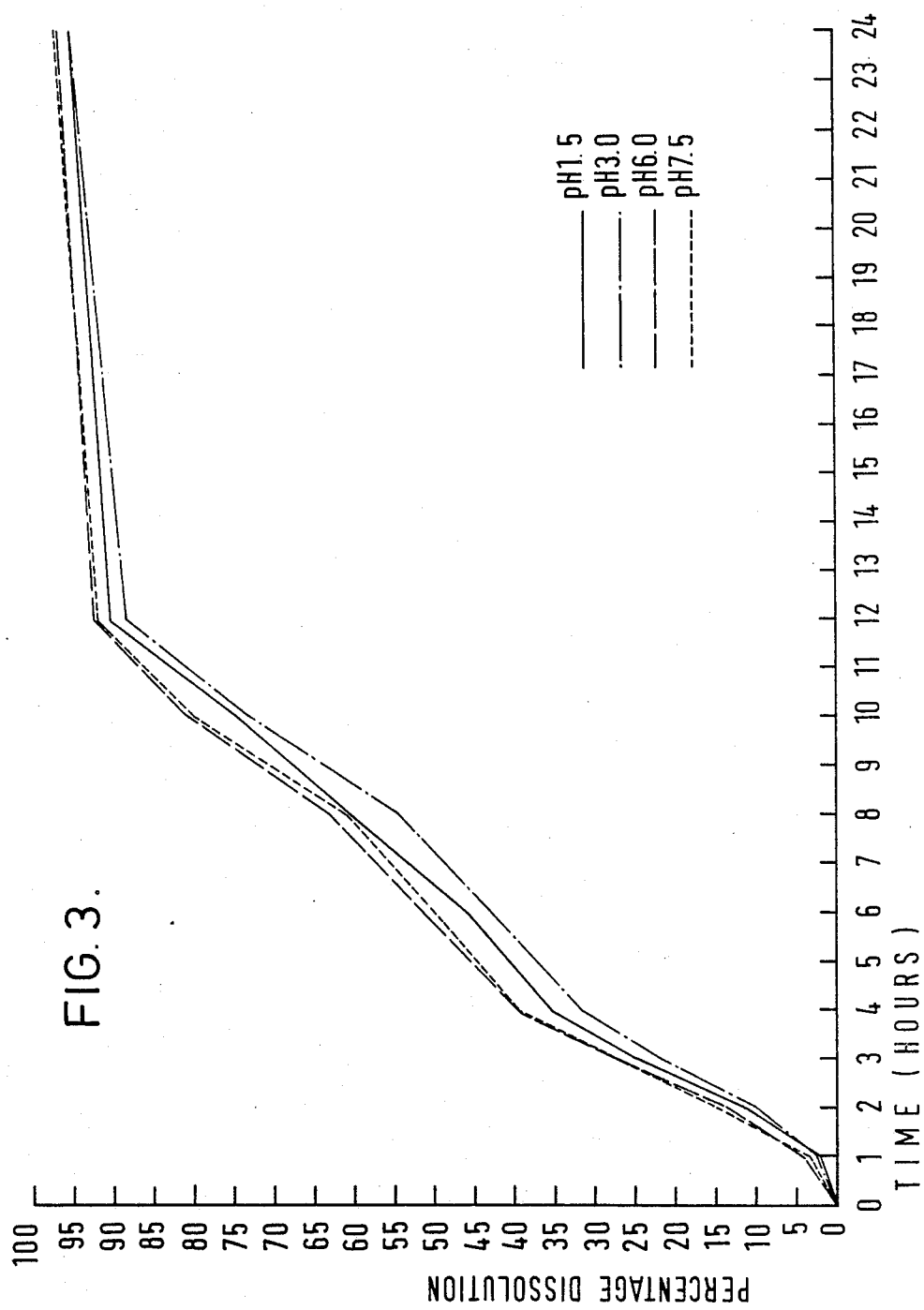

The dissolution rate of the pellets was measured according to the procedure set forth in Example 1. Again the dissolution test was carried out using solutions of pH 1.5, 3.0, 6.0 and 7.5 to determine the degree of pH dependence. The results are given in Table 3. A graphic representation of the results is shown in FIG. 3 of the accompanying drawings.

TABLE 3
PELLETS OF EXAMPLE 2
PERCENTAGE DISSOLUTION TIME (HOURS)

| pH | 0.00 | 1.00 | 2.00 | 3.00 | 4.00 | 6.00 | 8.00 | 10.00 | 12.00 | 24.00 |
|---|---|---|---|---|---|---|---|---|---|---|
| pH 1.5 | 0.00 | 2.00 | 11.20 | 24.60 | 35.20 | 45.60 | 60.10 | 74.40 | 90.10 | 94.90 |
| pH 3.0 | 0.00 | 2.50 | 10.00 | 21.80 | 31.60 | 42.80 | 54.20 | 73.00 | 88.20 | 94.80 |
| pH 6.0 | 0.00 | 4.00 | 13.70 | 27.10 | 39.40 | 51.20 | 62.80 | 80.70 | 92.20 | 96.40 |
| pH 7.5 | 0.00 | 3.40 | 14.70 | 27.00 | 39.20 | 49.70 | 60.70 | 79.90 | 91.80 | 96.80 |
| MEAN | 0.00 | 2.98 | 12.40 | 25.13 | 36.35 | 47.32 | 59.45 | 77.00 | 98.57 | 95.73 |
| ST DEV | 0.00 | 0.90 | 2.17 | 2.50 | 3.71 | 3.83 | 3.69 | 3.87 | 1.83 | 1.02 |
| *CV (%) | 0.00 | 30.11 | 17.53 | 9.95 | 10.21 | 8.10 | 6.20 | 5.02 | 2.02 | 1.07 |

*Coefficient of variation

EXAMPLE 3

Pellets prepared according to Example 1 were filled directed into hard gelatine capsules without the addition of any extra ingredients so as to obtain capsules containing 300 mg of quinidine sulphate.

EXAMPLE 4

Pellets prepared according to Example 2 were filled directly into hard gelatin capsules without the addition of any extra ingredients so as to obtain capsules containing 600 mg of quinidine sulphate.

BIOAVAILABILITY DATA

Figure 4:
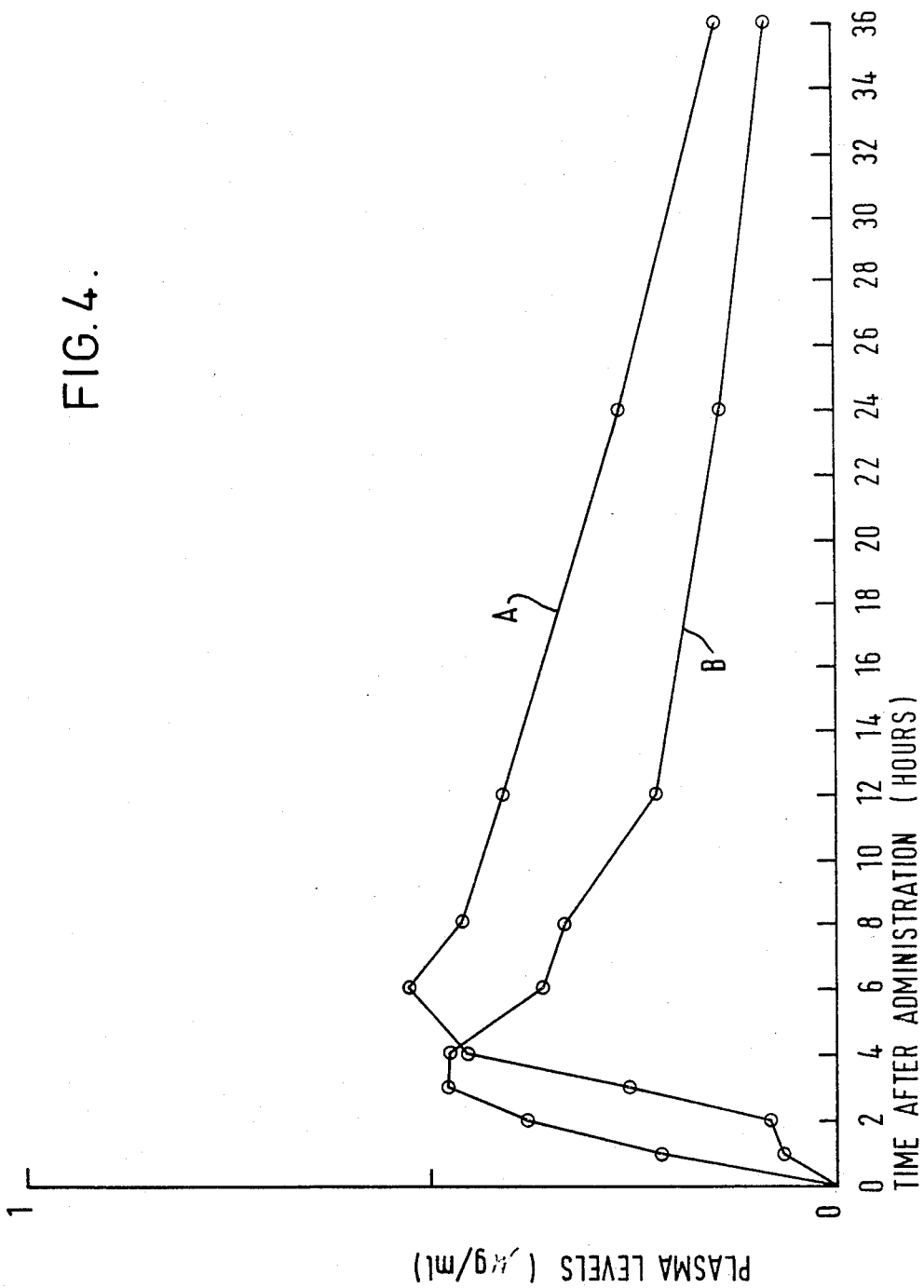

FIG. 4 is a graph of plasma levels (μg/ml) versus time after administration (hour) for a single dose (300 mg) of quinidine sulphate in capsule form prepared in Example 3 (A) compared with a single dose (300 mg) of Quinidex Extentabs (Quinidex Extentabs is a Trade Mark of A. H. Robins & Co. Inc.,) tablets (B). The graphs of FIG. 4 were drawn from the mean values obtained for 6 subjects according to the data listed in Tables 4 and 5.

TABLE 4

BLOOD LEVEL STUDY RESULTS - SUMMARY OF STATISTICS
QUINIDINE SULPHATE CAPSULE OF EXAMPLE 3 PLASMA LEVELS (μg/ml)

| SUBJ | \multicolumn{10}{c}{TIME AFTER ADMINISTRATION (HOURS)} | |
|---|---|---|---|---|---|---|---|---|---|---|
|  | 0.00 | 1.00 | 2.00 | 3.00 | 4.00 | 6.00 | 8.00 | 12.00 | 24.00 | 36.00 | AUC.** |
| 1 | 0.00 | 0.09 | 0.11 | 0.17 | 0.19 | 0.23 | 0.26 | 0.25 | 0.24 | 0.10 | 7.38 |
| 2 | 0.00 | 0.01 | 0.03 | 0.07 | 0.26 | 0.46 | 0.57 | 0.58 | 0.33 | 0.14 | 12.57 |
| 3 | 0.00 | 0.09 | 0.10 | 0.50 | 0.88 | 0.91 | 0.69 | 0.55 | 0.52 | 0.30 | 18.34 |
| 4 | 0.00 | 0.10 | 0.13 | 0.35 | 0.40 | 0.41 | 0.21 | 0.21 | 0.07 | 0.10 | 5.75 |
| 5 | 0.00 | 0.08 | 0.08 | 0.07 | 0.35 | 0.47 | 0.46 | 0.36 | 0.12 | 0.04 | 7.64 |
| 6 | 0.00 | 0.02 | 0.03 | 0.37 | 0.65 | 0.68 | 0.58 | 0.51 | 0.31 | 0.18 | 13.38 |
| MEAN | 0.00 | 0.07 | 0.08 | 0.26 | 0.46 | 0.53 | 0.46 | 0.41 | 0.27 | 0.14 | 10.84 |
| STD DEV | 0.00 | 0.04 | 0.04 | 0.18 | 0.26 | 0.24 | 0.19 | 0.16 | 0.16 | 0.09 | 4.77 |
| *CV (%) | 0.00 | 60.57 | 52.44 | 69.70 | 57.39 | 44.91 | 41.31 | 38.81 | 61.07 | 62.66 | 44.02 |
| MAX. | 0.00 | 0.10 | 0.13 | 0.50 | 0.88 | 0.91 | 0.69 | 0.58 | 0.62 | 0.30 | 18.34 |
| MIN. | 0.00 | 0.01 | 0.03 | 0.07 | 0.19 | 0.23 | 0.21 | 0.21 | 0.07 | 0.04 | 5.75 |

| MEAN OF CV VALUES AT SAMPLE POINTS | NUMBER OF ZERO BLOOD LEVELS | NUMBER OF POOR ABSORBERS <10% AUC | C (MAX)/ C (MIN). AT 36 HOURS |
|---|---|---|---|
| 54.32 | 0. | 0. | 3.67 |

| SUBJ. | \multicolumn{4}{c}{HOURS COVER AT FOUR BLOOD LEVELS} | PEAKING TIME | PEAK HEIGHT |
|---|---|---|---|---|---|---|
|  | 0.00 | 0.10 | 0.20 | 0.30 |  |  |
| 1 | 36.00 | 34.50 | 22.93 | 0.00 | 8.00 | 0.26 |
| 2 | 36.00 | 32.84 | 28.53 | 21.49 | 12.00 | 0.58 |
| 3 | 36.00 | 34.00 | 33.75 | 33.50 | 6.00 | 0.91 |
| 4 | 36.00 | 20.43 | 10.54 | 4.33 | 6.00 | 0.41 |
| 5 | 36.00 | 23.89 | 16.54 | 11.18 | 6.00 | 0.47 |
| 6 | 36.00 | 33.79 | 31.65 | 22.13 | 6.00 | 0.68 |
| MEAN | 36.00 | 29.91 | 23.99 | 15.44 | 7.33 | 0.55 |
| \multicolumn{7}{c}{BASED ON MEAN BLOOD LEVEL CURVE} |
| MEAN | 36.00 | 33.89 | 27.73 | 17.88 | 6.00 | 0.53 |

CUMULATIVE DISTRIBUTION OF AUC

|  | \multicolumn{10}{c}{HOURS AFTER ADMINISTRATION} |
|---|---|---|---|---|---|---|---|---|---|---|
|  | 0.00 | 1.00 | 2.00 | 3.00 | 4.00 | 6.00 | 8.00 | 12.00 | 24.00 | 36.00. |
| MEAN | 0.00 | 0.03 | 0.11 | 0.27 | 0.63 | 1.61 | 2.60 | 4.34 | 8.39 | 10.84 |

CUMULATIVE PERCENTAGE AUC

|  | \multicolumn{10}{c}{HOURS AFTER ADMINISTRATION} |
|---|---|---|---|---|---|---|---|---|---|---|
|  | 0.00 | 1.00 | 2.00 | 3.00 | 4.00 | 6.00 | 8.00 | 12.00 | 24.00 | 36.00 |
| MEAN | 0.00 | 0.39 | 1.27 | 3.04 | 6.47 | 15.79 | 25.12 | 41.46 | 78.46 | 100.00 |

DISTRIBUTION OF AUC

|  | \multicolumn{10}{c}{HOURS AFTER ADMINISTRATION} |
|---|---|---|---|---|---|---|---|---|---|---|
|  | 0.00 | 1.00 | 2.00 | 3.00 | 4.00 | 6.00 | 8.00 | 12.00 | 24.00 | 36.00 |
| MEAN | 0.00 | 0.03 | 0.07 | 0.17 | 0.36 | 0.98 | 0.99 | 1.74 | 4.05 | 2.45 |

DISTRIBUTION OF PERCENTAGE AUC

|  | \multicolumn{10}{c}{HOURS AFTER ADMINISTRATION} |
|---|---|---|---|---|---|---|---|---|---|---|
|  | 0.00 | 1.00 | 2.00 | 3.00 | 4.00 | 6.00 | 8.00 | 12.00 | 24.00 | 36.00 |
| MEAN | 0.00 | 0.39 | 0.88 | 1.76 | 3.43 | 9.33 | 9.32 | 16.34 | 37.01 | 21.54 |

*Coefficient of variation
**Area under curve

TABLE 5

BLOOD LEVEL STUDY RESULTS - SUMMARY OF STATISTICS
REFERENCE-QUINIDEX EXTENTABS (300 mg)
PLASMA LEVELS (μg/ml)

| SUBJ | \multicolumn{10}{c}{TIME AFTER ADMINISTRATION (HOURS)} | |
|---|---|---|---|---|---|---|---|---|---|---|
|  | 0.00 | 1.00 | 2.00 | 3.00 | 4.00 | 6.00 | 8.00 | 12.00 | 24.00 | 36.00 | AUC.** |
| 1 | 0.00 | 0.40 | 0.35 | 0.33 | 0.32 | 0.24 | 0.22 | 0.20 | 0.11 | 0.06 | 5.98 |
| 2 | 0.00 | 0.10 | 0.21 | 0.33 | 0.30 | 0.31 | 0.24 | 0.16 | 0.06 | 0.03 | 4.61 |
| 3 | 0.00 | 0.21 | 0.46 | 0.73 | 0.54 | 0.51 | 0.67 | 0.37 | 0.29 | 0.13 | 12.46 |
| 4 | 0.00 | 0.23 | 0.44 | 0.64 | 0.59 | 0.32 | 0.21 | 0.10 | 0.09 | 0.09 | 5.89 |
| 5 | 0.00 | 0.16 | 0.39 | 0.41 | 0.40 | 0.33 | 0.26 | 0.17 | 0.11 | 0.06 | 0.04 |
| 6 | 0.00 | 0.19 | 0.44 | 0.44 | 0.71 | 0.46 | 0.40 | 0.33 | 0.18 | 0.13 | 9.84 |

TABLE 5-continued
BLOOD LEVEL STUDY RESULTS - SUMMARY OF STATISTICS
REFERENCE-QUINIDEX EXTENTABS (300 mg)
PLASMA LEVELS (μg/ml)

| MEAN    | 0.00 | 0.22  | 0.38  | 0.48  | 0.48  | 0.36  | 0.33  | 0.22  | 0.14  | 0.08  | 7.47  |
|---------|------|-------|-------|-------|-------|-------|-------|-------|-------|-------|-------|
| STD DEV | 0.00 | 0.10  | 0.09  | 0.17  | 0.16  | 0.10  | 0.18  | 0.11  | 0.08  | 0.04  | 3.01  |
| *CV (%) | 0.00 | 47.14 | 24.43 | 34.81 | 34.21 | 28.17 | 53.65 | 47.52 | 59.59 | 48.99 | 40.37 |
| MAX.    | 0.00 | 0.40  | 0.46  | 0.73  | 0.71  | 0.51  | 0.67  | 0.37  | 0.29  | 0.13  | 12.46 |
| MIN.    | 0.00 | 0.10  | 0.21  | 0.33  | 0.30  | 0.24  | 0.21  | 0.10  | 0.06  | 0.03  | 4.61  |

| MEAN OF CV VALUES AT SAMPLE POINTS | NUMBER OF ZERO BLOOD LEVELS | NUMBER OF POOR ABSORBERS <10% AUC | C (MAX)/C (MIN). AT 36 HOURS |
|---|---|---|---|
| 42.06 | 0. | 0. | 5.76 |

| SUBJ. | HOURS COVER AT FOUR BLOOD LEVELS | | | | PEAKING TIME | PEAK HEIGHT |
|---|---|---|---|---|---|---|
|   | 0.00 | 0.10 | 0.20 | 0.30 | | |
| 1 | 36.00 | 26.15 | 11.50 | 3.75 | 1.00 | 0.40 |
| 2 | 36.00 | 18.20 | 8.09 | 3.54 | 3.00 | 0.33 |
| 3 | 36.00 | 35.52 | 29.80 | 21.14 | 3.00 | 0.73 |
| 4 | 36.00 | 11.57 | 7.49 | 5.03 | 3.00 | 0.64 |
| 5 | 36.00 | 25.78 | 9.49 | 5.25 | 3.00 | 0.41 |
| 6 | 36.00 | 35.47 | 21.36 | 12.96 | 4.00 | 0.71 |
| MEAN | 36.00 | 25.45 | 14.62 | 8.61 | 2.83 | 0.54 |
| | BASED ON MEAN BLOOD LEVEL CURVE | | | | | |
| MEAN | 36.00 | 32.01 | 14.25 | 7.68 | 3.00 | 0.48 |

CUMULATIVE DISTRIBUTION OF AUC
HOURS AFTER ADMINISTRATION

|      | 0.00 | 1.00 | 2.00 | 3.00 | 4.00 | 6.00 | 8.00 | 12.00 | 24.00 | 36.00 |
|------|------|------|------|------|------|------|------|-------|-------|-------|
| MEAN | 0.00 | 0.11 | 0.41 | 0.84 | 1.32 | 2.15 | 2.85 | 3.96  | 6.13  | 7.47  |

CUMULATIVE PERCENTAGE AUC
HOURS AFTER ADMINISTRATION

|      | 0.00 | 1.00 | 2.00 | 3.00  | 4.00  | 6.00  | 8.00  | 12.00 | 24.00 | 36.00  |
|------|------|------|------|-------|-------|-------|-------|-------|-------|--------|
| MEAN | 0.00 | 1.59 | 5.88 | 11.98 | 18.71 | 30.45 | 39.89 | 54.51 | 82.81 | 100.00 |

DISTRIBUTION OF AUC
HOURS AFTER ADMINISTRATION

|      | 0.00 | 1.00 | 2.00 | 3.00 | 4.00 | 6.00 | 8.00 | 12.00 | 24.00 | 36.00 |
|------|------|------|------|------|------|------|------|-------|-------|-------|
| MEAN | 0.00 | 0.11 | 0.30 | 0.43 | 0.48 | 0.84 | 0.70 | 1.11  | 2.17  | 1.34  |

DISTRIBUTION OF PERCENTAGE AUC
HOURS AFTER ADMINISTRATION

|      | 0.00 | 1.00 | 2.00 | 3.00 | 4.00 | 6.00  | 8.00 | 12.00 | 24.00 | 36.00 |
|------|------|------|------|------|------|-------|------|-------|-------|-------|
| MEAN | 0.00 | 1.59 | 4.30 | 6.10 | 6.73 | 11.74 | 9.44 | 14.62 | 28.30 | 17.19 |

*Coefficient of variation
**Area under curve

Figure 5:
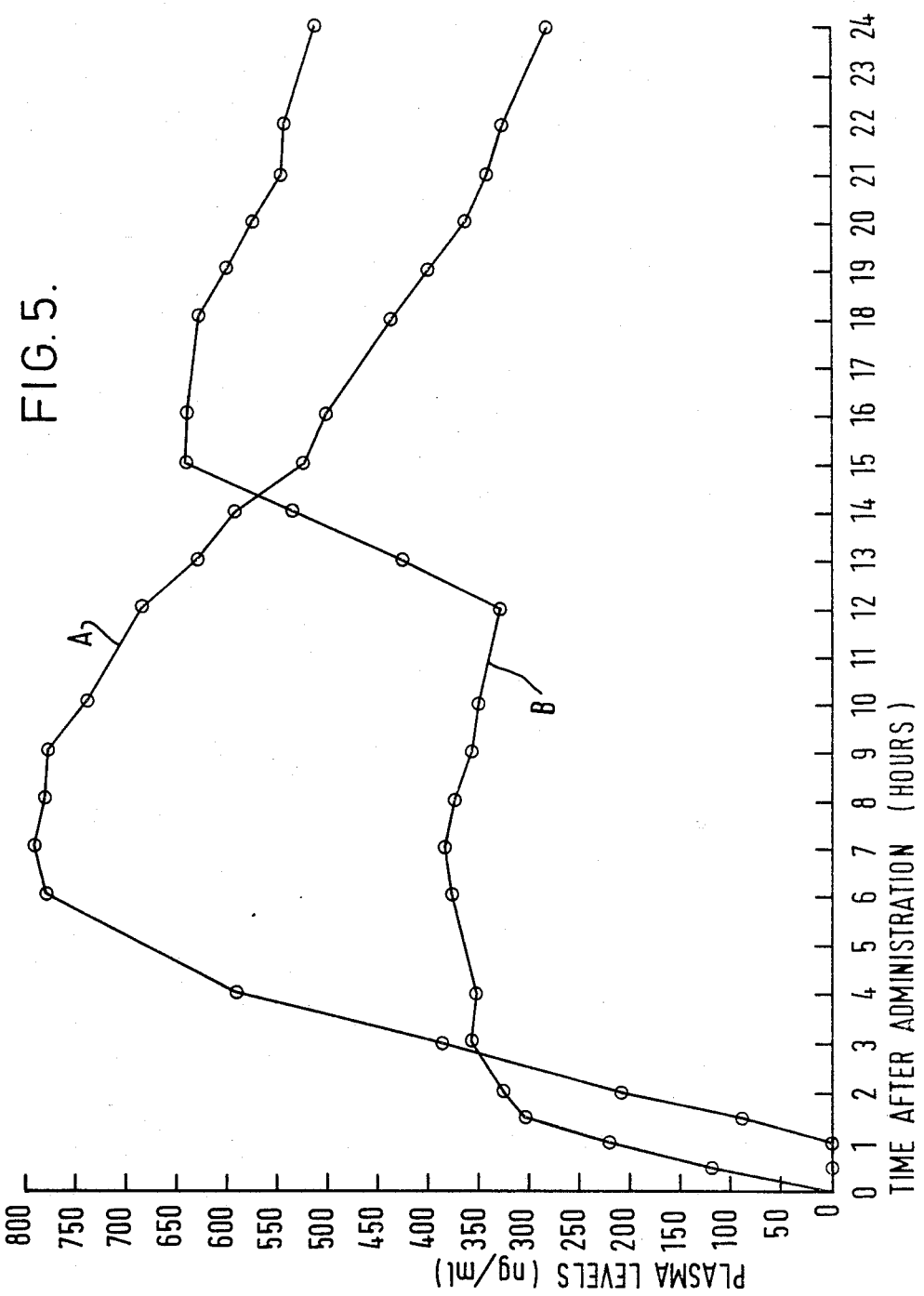

FIG. 5 is a graph of plasma levels (ng/ml) versus time after administration (hours) for a single dose (600 mg) of quinidine sulphate capsules prepared according to Example 4 (A) compared with a single dose (300 mg) of Quinidex Extentabs tablets (B). The graphs of FIG. 5 are drawn from the mean values obtained for six subjects according to the data listed in Tables 6 and 7.

FIG. 6 is a graph of percentage dissolution versus time. Curve B shows the maximum percentage dissolution per unit time and curve A the minimum percentage dissolution per unit time permissible to achieve the desired plasma concentration. The graphs of FIG. 6 were drawn from the mean values obtained for one subject.

The controlled absorption quinidine sulphate according to the invention at single-doses of 300 mg (Example 3) and 600 mg (Example 4) had an equivalent or superior plasma level AUC (10.8 and 14.6 μg×h/ml, respectively) compared with the reference, Quinidex Extentabs (7.5 and 15.6 μg×h/ml, for single-dose and double-dose, respectively).

The controlled absorption quinidine sulphate capsules of Examples 3 and 4 showed peak plasma levels similar (0.55 and 0.84 μg/ml, respectively) to those of Quinidex Extentabs (0.54 and 0.70 μg/ml, for single-dose and double-dose, respectively). Whereas the Quinidex Extentabs showed peak plasma levels at 2.8 hours, the controlled absorption quinidine sulphate capsules of Examples 3 and 4 resulted in delayed peak plasma levels at 7.33 hours.

In terms of variability, the quinidine sulphate capsules of Examples 3 and 4 were similar to Quinidex Extentabs used as reference as shown by the CV % figures in Tables 4, 5, 6 and 7.

The results of the bioavailability studies show that the controlled absorption quinidine formulation according to the invention is an effective once daily form of quinidine, as demonstrated by good bioavailability, delayed peaking time and prolonged effective plasma levels through to 24 hours after administration.

TABLE 6

BLOOD LEVEL STUDY RESULTS - SUMMARY OF STATISTICS
QUINIDINE SULPHATE CAPSULE OF EXAMPLE 4
PLASMA LEVELS (μg/ml)

| SUBJ. | 0.00 | 0.50 | 1.00 | 1.50 | 2.00 | 3.00 | 4.00 | 6.00 | 7.00 | 8.00 | 9.00 | 10.00 | 12.00 | 13.00 |
|---|---|---|---|---|---|---|---|---|---|---|---|---|---|---|
| 1 | 0.00 | 0.00 | 0.00 | 0.00 | 0.16 | 0.37 | 0.49 | 0.69 | 0.76 | 0.65 | 0.68 | 0.61 | 0.58 | 0.56 |
| 2 | 0.00 | 0.00 | 0.00 | 0.00 | 0.14 | 0.26 | 0.45 | 0.73 | 0.76 | 0.80 | 0.86 | 0.88 | 0.88 | 0.81 |
| 3 | 0.00 | 0.00 | 0.00 | 0.00 | 0.10 | 0.24 | 0.43 | 0.59 | 0.60 | 0.66 | 0.63 | 0.59 | 0.53 | 0.43 |
| 4 | 0.00 | 0.00 | 0.00 | 0.10 | 0.18 | 0.42 | 0.70 | 0.98 | 1.02 | 0.97 | 0.99 | 0.90 | 0.82 | 0.67 |
| 5 | 0.00 | 0.00 | 0.00 | 0.23 | 0.33 | 0.45 | 0.71 | 0.73 | 0.66 | 0.66 | 0.63 | 0.58 | 0.54 | 0.61 |
| 6 | 0.00 | 0.00 | 0.00 | 0.29 | 0.34 | 0.57 | 0.76 | 0.95 | 0.95 | 0.95 | 0.88 | 0.88 | 0.76 | 0.79 |
| MEAN | 0.00 | 0.00 | 0.00 | 0.09 | 0.21 | 0.39 | 0.59 | 0.78 | 0.79 | 0.78 | 0.78 | 0.74 | 0.69 | 0.63 |
| ST DEV | 0.00 | 0.00 | 0.00 | 0.11 | 0.10 | 0.12 | 0.15 | 0.16 | 0.16 | 0.15 | 0.15 | 0.16 | 0.15 | 0.13 |
| *CV (%) | 0.00 | 0.00 | 0.00 | 199.90 | 49.80 | 32.14 | 25.21 | 19.99 | 20.62 | 19.07 | 19.53 | 21.77 | 22.42 | 20.60 |
| MAX | 0.00 | 0.00 | 0.00 | 0.23 | 0.34 | 0.57 | 0.76 | 0.98 | 1.02 | 0.97 | 0.99 | 0.90 | 0.88 | 0.81 |
| MIN | 0.00 | 0.00 | 0.00 | 0.00 | 0.10 | 0.24 | 0.43 | 0.59 | 0.60 | 0.65 | 0.63 | 0.58 | 0.53 | 0.43 |

| MEAN OF CV VALUES AT SAMPLE POINTS | NUMBER OF ZERO BLOOD LEVELS | NUMBER OF POOR ABSORBERS <10% AUC | C(MAX)/C(MIN) AT 24 HOURS |
|---|---|---|---|
| 38.62 | 24 | 0 | 2.81 |

| SUBJ. | 14.00 | 15.00 | 16.00 | 18.00 | 19.00 | 20.00 | 21.00 | 22.00 | 24.00 | 30.00 | 36.00 | 48.00 | AUC** |
|---|---|---|---|---|---|---|---|---|---|---|---|---|---|
| 1 | 0.57 | 0.56 | 0.58 | 0.46 | 0.44 | 0.41 | 0.38 | 0.39 | 0.32 | 0.21 | 0.11 | 0.00 | 14.73 |
| 2 | 0.66 | 0.57 | 0.63 | 0.55 | 0.49 | 0.45 | 0.41 | 0.37 | 0.30 | 0.19 | 0.12 | 0.00 | 16.33 |
| 3 | 0.42 | 0.36 | 0.32 | 0.27 | 0.24 | 0.22 | 0.23 | 0.23 | 0.16 | 0.00 | 0.00 | 0.00 | 9.19 |
| 4 | 0.59 | 0.52 | 0.48 | 0.51 | 0.48 | 0.43 | 0.38 | 0.35 | 0.27 | 0.17 | 0.00 | 0.00 | 15.86 |
| 5 | 0.58 | 0.51 | 0.49 | 0.44 | 0.38 | 0.34 | 0.35 | 0.32 | 0.35 | 0.21 | 0.15 | 0.10 | 15.86 |
| 6 | 0.73 | 0.62 | 0.51 | 0.39 | 0.37 | 0.33 | 0.30 | 0.28 | 0.29 | 0.13 | 0.00 | 0.00 | 15.50 |
| MEAN | 0.59 | 0.52 | 0.50 | 0.44 | 0.40 | 0.36 | 0.34 | 0.32 | 0.28 | 0.15 | 0.06 | 0.02 | 14.58 |
| ST DEV | 0.10 | 0.09 | 0.11 | 0.10 | 0.09 | 0.09 | 0.07 | 0.06 | 0.07 | 0.08 | 0.07 | 0.04 | 2.70 |
| *CV (%) | 17.55 | 17.03 | 21.15 | 22.61 | 23.18 | 23.46 | 19.36 | 19.52 | 23.27 | 52.82 | 111.50 | 244.95 | 18.49 |
| MAX | 0.73 | 0.62 | 0.63 | 0.55 | 0.49 | 0.45 | 0.41 | 0.39 | 0.35 | 0.21 | 0.15 | 0.10 | 16.33 |
| MIN | 0.42 | 0.36 | 0.32 | 0.27 | 0.24 | 0.22 | 0.23 | 0.23 | 0.16 | 0.00 | 0.00 | 0.00 | 9.19 |

| MEAN OF CV VALUES AT SAMPLE POINTS | NUMBER OF ZERO BLOOD LEVELS | NUMBER OF POOR ABSORBERS <10% AUC | C(MAX)/C(MIN)/AT 24 HOURS |
|---|---|---|---|
| 38.62 | 24 | 0 | 2.81 |

| SUBJ. | HOURS COVER AT FOUR BLOOD LEVELS | | | | PEAKING TIME | PEAK HEIGHT |
|---|---|---|---|---|---|---|
| | 0.00 | 0.20 | 0.40 | 0.60 | | |
| 1 | 46.50 | 28.41 | 17.08 | 5.57 | 7.00 | 0.76 |
| 2 | 46.50 | 26.95 | 17.51 | 10.85 | 10.00 | 0.88 |
| 3 | 23.50 | 20.14 | 10.49 | 2.75 | 8.00 | 0.66 |
| 4 | 35.00 | 26.12 | 17.68 | 10.23 | 7.00 | 1.02 |
| 5 | 47.00 | 29.57 | 16.08 | 6.50 | 6.00 | 0.73 |
| 6 | 35.00 | 25.88 | 15.57 | 12.02 | 6.00 | 0.96 |
| MEAN | 39.75 | 26.18 | 15.74 | 2.99 | 7.33 | 0.84 |
| | BASED ON MEAN BLOOD LEVEL CURVE | | | | | |
| MEAN | 47.00 | 25.90 | 15.93 | 9.68 | 7.00 | 0.29 |

*Coefficient of variation
**Area under curve

TABLE 7

BLOOD LEVEL STUDY RESULTS - SUMMARY OF STATISTICS
REFERENCE QUINIDEX EXTENTABS (300 mg)
PLASMA LEVELS (μg/ml)

| SUBJ. | 0.00 | 0.50 | 1.00 | 1.50 | 2.00 | 3.00 | 4.00 | 6.00 | 7.00 | 8.00 | 9.00 | 10.00 | 12.00 | 13.00 |
|---|---|---|---|---|---|---|---|---|---|---|---|---|---|---|
| 1 | 0.00 | 0.16 | 0.26 | 0.29 | 0.29 | 0.32 | 0.28 | 0.38 | 0.40 | 0.38 | 0.33 | 0.35 | 0.34 | 0.52 |
| 2 | 0.00 | 0.11 | 0.24 | 0.29 | 0.25 | 0.28 | 0.24 | 0.25 | 0.27 | 0.26 | 0.28 | 0.31 | 0.24 | 0.48 |
| 3 | 0.00 | 0.14 | 0.20 | 0.21 | 0.21 | 0.22 | 0.21 | 0.25 | 0.24 | 0.26 | 0.30 | 0.32 | 0.27 | 0.23 |
| 4 | 0.00 | 0.00 | 0.20 | 0.25 | 0.28 | 0.32 | 0.30 | 0.34 | 0.40 | 0.41 | 0.39 | 0.37 | 0.36 | 0.35 |
| 5 | 0.00 | 0.30 | 0.42 | 0.43 | 0.44 | 0.43 | 0.42 | 0.38 | 0.37 | 0.39 | 0.34 | 0.31 | 0.38 | 0.63 |
| 6 | 0.00 | 0.00 | 0.00 | 0.35 | 0.48 | 0.57 | 0.66 | 0.66 | 0.62 | 0.54 | 0.50 | 0.44 | 0.38 | 0.34 |
| MEAN | 0.00 | 0.12 | 0.22 | 0.30 | 0.33 | 0.36 | 0.35 | 0.38 | 0.38 | 0.37 | 0.36 | 0.35 | 0.33 | 0.43 |
| ST DEV | 0.00 | 0.11 | 0.14 | 0.08 | 0.11 | 0.13 | 0.17 | 0.15 | 0.13 | 0.11 | 0.08 | 0.06 | 0.17 | 0.14 |
| *CV (%) | 0.00 | 95.07 | 61.39 | 25.59 | 33.52 | 35.05 | 47.60 | 40.04 | 35.03 | 28.13 | 22.34 | 14.34 | 18.11 | 34.09 |
| MAX | 0.00 | 0.30 | 0.42 | 0.43 | 0.48 | 0.57 | 0.66 | 0.66 | 0.62 | 0.54 | 0.50 | 0.44 | 0.38 | 0.63 |
| MIN | 0.00 | 0.00 | 0.00 | 0.21 | 0.21 | 0.22 | 0.21 | 0.25 | 0.24 | 0.26 | 0.28 | 0.31 | 0.24 | 0.23 |

| SUBJ. | 14.00 | 15.00 | 16.00 | 18.00 | 19.00 | 20.00 | 21.00 | 22.00 | 24.00 | 30.00 | 36.00 | 48.00 | AUC** |
|---|---|---|---|---|---|---|---|---|---|---|---|---|---|

TABLE 7-continued

BLOOD LEVEL STUDY RESULTS - SUMMARY OF STATISTICS
REFERENCE QUINIDEX EXTENTABS (300 mg)
PLASMA LEVELS (μg/ml)

| | | | | | | | | | | | | | |
|---|---|---|---|---|---|---|---|---|---|---|---|---|---|
| 1 | 0.62 | 0.72 | 0.68 | 0.60 | 0.58 | 0.56 | 0.49 | 0.51 | 0.37 | 0.32 | 0.17 | 0.00 | 15.13 |
| 2 | 0.57 | 0.65 | 0.58 | 0.73 | 0.61 | 0.60 | 0.56 | 0.55 | 0.55 | 0.31 | 0.16 | 0.00 | 14.92 |
| 3 | 0.26 | 0.37 | 0.43 | 0.36 | 0.40 | 0.43 | 0.46 | 0.49 | 0.48 | 0.29 | 0.12 | 0.00 | 11.84 |
| 4 | 0.42 | 0.60 | 0.67 | 0.58 | 0.57 | 0.54 | 0.51 | 0.51 | 0.49 | 0.35 | 0.18 | 0.00 | 15.32 |
| 5 | 0.72 | 0.69 | 0.63 | 0.65 | 0.60 | 0.51 | 0.49 | 0.47 | 0.52 | 0.29 | 0.15 | 0.00 | 16.10 |
| 6 | 0.62 | 0.82 | 0.85 | 0.85 | 0.84 | 0.81 | 0.77 | 0.73 | 0.67 | 0.34 | 0.16 | 0.00 | 19.98 |
| MEAN | 0.54 | 0.64 | 0.64 | 0.63 | 0.60 | 0.58 | 0.55 | 0.51 | 0.32 | 0.16 | 0.00 | 15.55 | |
| ST DEV | 0.17 | 0.15 | 0.14 | 0.16 | 0.14 | 0.13 | 0.11 | 0.10 | 0.10 | 0.03 | 0.02 | 0.00 | 2.62 |
| *CV (%) | 31.14 | 23.73 | 21.47 | 26.16 | 23.45 | 22.35 | 20.91 | 17.53 | 19.11 | 7.91 | 13.18 | 0.00 | 16.86 |
| MAX | 0.72 | 0.82 | 0.85 | 0.85 | 0.84 | 0.81 | 0.77 | 0.73 | 0.67 | 0.35 | 0.18 | 0.00 | 19.98 |
| MIN | 0.26 | 0.37 | 0.43 | 0.36 | 0.40 | 0.43 | 0.46 | 0.47 | 0.37 | 0.29 | 0.12 | 0.00 | 11.84 |

| MEAN OF CV VALUES AT SAMPLE POINTS | NUMBER OF ZERO BLOOD LEVELS | NUMBER OF POOR ABSORBERS <10% AUC | C(MAX)/C(MIN) AT 24 HOURS |
|---|---|---|---|
| 38.69 | 8 | 0. | 1.25 |

| | HOURS COVER AT FOUR BLOOD LEVELS | | | | PEAKING | PEAK |
|---|---|---|---|---|---|---|
| SUBJ. | 0.00 | 0.20 | 0.40 | 0.60 | TIME | HEIGHT |
| 1 | 48.00 | 34.10 | 11.24 | 4.20 | 15.00 | 0.72 |
| 2 | 48.00 | 33.55 | 15.08 | 5.07 | 18.00 | 0.73 |
| 3 | 48.00 | 32.18 | 8.88 | 0.00 | 22.00 | 0.49 |
| 4 | 47.50 | 34.29 | 15.64 | 2.56 | 16.00 | 0.67 |
| 5 | 48.00 | 33.52 | 19.13 | 6.12 | 14.00 | 0.72 |
| 6 | 47.00 | 33.38 | 25.34 | 15.26 | 16.00 | 0.85 |
| MEAN | 47.75 | 33.50 | 15.89 | 5.53 | 16.83 | 0.70 |
| | BASED ON MEAN BLOOD LEVEL CURVE | | | | | |
| MEAN | 49.00 | 33.47 | 14.72 | 4.39 | 15.00 | 0.64 |

*Coefficient of variation
**Area under curve

What we claim is:

1. A controlled absorption quinidine pellet formulation for oral administration comprising:
   (i) a core of
      (a) a powder mixture comprising quinidine or a pharmaceutically acceptable salt thereof and an -organic acid selected from the group consisting of adipic acid, ascorbic acid, citric acid, fumaric acid, malic acid, succinic acid and tartaric acid or a mixture thereof, and
      (b) a polymeric material comprising a major proportion of a pharmaceutically acceptable water-soluble polymer and a minor proportion of a pharmaceutically acceptable water-insoluble polymer, said core comprising layers of said powder mixture and said polymeric material superimposed one upon the other and said polymeric material being present in an amount effective to ensure that all of said powder mixture is coated into said core; and
   (ii) a multi-layer membrane surrounding said core and containing a major proportion of a pharmaceutically acceptable film-forming, water-insoluble polymer and a minor proportion of a pharmaceutically acceptable film-forming, water-soluble polymer,
   the number of layers in said membrane and the ratio of said water-soluble polymer to said water-insoluble polymer being effective to permit release of said quinidine from said pellet at a rate allowing controlled absorption thereof over a twenty-four hour period following oral administration, said rate being measured in vitro as a dissolution rate of said pellet which is substantially pH independent and which, when measured in a Basket Assembly according to U.S. Pharmacopoeia XXI at 37° C. and 75 r.p.m., substantially corresponds to the following:
   (a) from 0 to 15% of the total quinidine is released after one hour of measurement in said assembly;
   (b) from 30 to 50% of the total quinidine is released after four hours of measurement in said assembly;
   (c) from 55 to 80% of the total quinidine is released after eight hours of measurement in said assembly; and
   (d) not less than 90% of the total quinidine is released after twenty-four hours of measurement in said assembly.

2. A pellet formulation according to claim 1, wherein the quinidine or pharmaceutically acceptable salt thereof and organic acid are present in a ratio of from 1:1 to 10:1.

3. A pellet formulation according to claim 1, wherein the water-soluble polymer of the core is selected from the group consisting of hydroxypropylmethylcellulose and polyvinylpyrrolidone.

4. A pellet formulation according to claim 1, wherein the water-insoluble polymer of the core is selected from the group consisting of methylcellulose, ethylcellulose, propylcellulose and shellac.

5. A pellet formulation according to claim 1, wherein the polymeric material of the core comprises a major proportion of a copolymer of acrylic and methacrylic acid esters which is freely permeable to water and a minor proportion of a copolymer of acrylic and methacrylic acid esters which is slightly permeable to water, the ratio of freely permeable to slightly permeable copolymer being determined by the inherent permeability of the respective polymers.

6. A pellet formulation according to claim 1, wherein the quinidine or pharmaceutically acceptable salt thereof, organic acid and polymeric material are built up on an inert core.

7. A pellet formulation according to claim 6, wherein the inert core is non-pareil seed having an average diameter of from 0.3 to 0.7 mm.

8. A pellet formulation according to claim 1, wherein the core includes one or more additional components selected from the group consisting of a lubricant, a dispersing agent and a surfactant.

9. A pellet formulation according to claim 1, wherein the water-insoluble polymer of the membrane is selected from the group consisting of shellac and ethylcellulose.

10. A pellet formulation according to claim 1, wherein the water-soluble polymer of the membrane is selected from the group consisting of polyvinylpyrrolidone and hydroxypropylmethylcellulose.

11. A pellet formulation according to claim 1, wherein the membrane is composed of a major proportion of a copolymer of acrylic and methacrylic acid esters which is slightly permeable to water and a minor proportion of a copolymer of acrylic and methacrylic acid esters which is freely permeable to water, the ratio of slightly permeable to freely permeable copolymer being determined by the inherent permeability of the respective polymers.

12. A pellet formulation according to claim 1, which contains quinidine sulphate as the active ingredient.

13. A process for the production of a pellet formulation according to claim 1, which comprises forming a core of quinidine or a pharmaceutically acceptable salt thereof and an organic acid and enclosing the core in a membrane of a film-forming polymer or mixture thereof which permits release of the quinidine or the pharmaceutically acceptable salt thereof in the manner set out in claim 1.

14. A capsule comprising pellets according to claim 1.

15. A tablet comprising pellets according to claim 1.

* * * * *